(12) United States Patent
Jansen et al.

(10) Patent No.: US 7,825,544 B2
(45) Date of Patent: Nov. 2, 2010

(54) COUPLING SYSTEM

(75) Inventors: Gerardus Lucien Mathildus Jansen, Eindhoven (NL); Marielle Johanna Langerak, Eindhoven (NL); Gijsbert Hobo, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 152 days.

(21) Appl. No.: 12/095,353

(22) PCT Filed: Nov. 29, 2006

(86) PCT No.: PCT/IB2006/054497

§ 371 (c)(1),
(2), (4) Date: May 29, 2008

(87) PCT Pub. No.: WO2007/063500

PCT Pub. Date: Jun. 7, 2007

(65) Prior Publication Data

US 2008/0303351 A1 Dec. 11, 2008

(30) Foreign Application Priority Data

Dec. 2, 2005 (EP) .................... 05111634

(51) Int. Cl.
*H01F 27/42* (2006.01)
(52) U.S. Cl. ...................... 307/104; 397/147
(58) Field of Classification Search .................. 307/104
See application file for complete search history.

(56) References Cited

U.S. PATENT DOCUMENTS 4,038,625 A  7/1977  Tompkins et al.

(Continued)

FOREIGN PATENT DOCUMENTS

DE   3720164 A1   12/1987

(Continued)

OTHER PUBLICATIONS

Barnard et al: "Optimized Linear Contactless Power Transmission Systems for Different Applications"; Proceedings of the 12TH Annual APEC'97 Conference in Atlanta, GA., Publication Date Feb. 23-27, 1997, IEEE vol. 2, pp. 953-959.

(Continued)

*Primary Examiner*—Robert L. DeBeradinis

(57) ABSTRACT

There is elucidated a device (10) comprising first and second magnetic cores (30, 40; 30a, 30b, 30c, 40a, 40b, 40c) forming a magnetic circuit. The circuit includes a first set of electrical windings (300, 310) for magnetically coupling a first electrical signal through the device (10) via a first magnetic path (350) in the circuit. The circuit includes a second set of electrical windings (400, 410) for magnetically coupling a second electrical signal through the device (10) via a second magnetic path (450) in the circuit. The paths (350, 450) are partially spatially intersecting. The sets of windings (300, 310, 400, 410) are configured so that: (a) the first set of windings (300, 310) is sensitive to magnetic flux in the first magnetic path (350), and insensitive to magnetic flux in the second magnetic path (450); and (b) the second set of windings (400, 410) is sensitive to magnetic flux in the second magnetic path (450), and insensitive to magnetic flux in the first magnetic path (350). The first and second cores (30, 40; 30a, 30b, 30c, 40a, 40b, 40c) enable relative motion (50) there between whilst coupling the signals through the circuit. The device (10) is beneficially employed in a medical system (800).

18 Claims, 5 Drawing Sheets

U.S. PATENT DOCUMENTS

| | | | |
|---|---|---|---|
| 4,953,123 | A | 8/1990 | Takeuchi et al. |
| 5,229,652 | A | 7/1993 | Hough |
| 5,264,776 | A | 11/1993 | Hulsey |
| 5,398,149 | A | 3/1995 | Weil |
| 5,528,113 | A | 6/1996 | Boys et al. |
| 5,659,909 | A | 8/1997 | Pfeuffer et al. |
| 6,032,546 | A * | 3/2000 | Stone .................. 74/5.7 |
| 6,331,744 | B1 | 12/2001 | Chen et al. |
| 6,414,578 | B1 * | 7/2002 | Jitaru .................. 336/170 |
| 6,686,823 | B2 | 2/2004 | Arntz et al. |
| 6,781,346 | B2 | 8/2004 | Reinhard et al. |
| 6,803,744 | B1 | 10/2004 | Sabo |
| 2002/0084698 | A1 | 7/2002 | Kelly et al. |
| 2003/0146062 | A1 | 8/2003 | Futschek |
| 2004/0142733 | A1 | 7/2004 | Parise |
| 2004/0218406 | A1 | 11/2004 | Jang et al. |
| 2005/0018452 | A1 | 1/2005 | Seo |
| 2005/0061191 | A1 | 3/2005 | Dietrich et al. |

FOREIGN PATENT DOCUMENTS

| | | |
|---|---|---|
| DE | 3802062 A1 | 8/1988 |
| DE | 19532296 A1 | 3/1997 |
| EP | 0314222 A1 | 5/1989 |
| EP | 0525459 A1 | 2/1993 |
| EP | 0878811 A2 | 11/1998 |
| EP | 1150314 A2 | 10/2001 |
| EP | 1176616 A2 | 1/2002 |
| NL | 1021561 C | 4/2004 |
| WO | WO0180442 A2 | 10/2001 |
| WO | WO0237641 A1 | 5/2002 |
| WO | WO03096512 A2 | 11/2003 |
| WO | WO2005015766 A1 | 2/2005 |
| WO | WO2005022692 A2 | 3/2005 |

OTHER PUBLICATIONS

Barnard et al: "Optimising Sliding Transformers for Contactless Power Transmission Systems"; 26TH Annual PESC'95 Conference in Atlanta, GA., IEEE, Publication Date Jun. 18-22, 1995, vol. 1, pp. 245-251.

Hatanaka et al: "Power Transmission of a Desk With a Cord-Free Power Supply"; IEEE Transactions on Magnetics, vol. 38, No. 5, Sep. 2002, pp. 3329-3331.

Murakami et al: "Consideration on Cordless Power Stateion—Contactless Power Transmission System"; IEEE Transactions on Magnetics, vol. 32, No. 5, Sep. 1996, pp. 5037-5039.

* cited by examiner

COUPLING SYSTEM

FIELD OF THE INVENTION

The present invention relates to coupling systems for concurrently conveying electrical power and data signals. Moreover, the present invention also relates to coupling devices operable to couple electrical power and data signals. Furthermore, the invention relates to methods of concurrently conveying electrical power and data signals. Additionally, the invention relates to apparatus including such coupling systems and devices.

BACKGROUND OF THE INVENTION

Many contemporary systems include configurations of electrical devices, which are operable to interact by way of information, and data exchange there between, but also need to be provided with electrical power to function. For example, contemporary computer systems often include several modules which are coup able to a computer back plane or mother board by way of electrical connectors; the electrical connectors include power lines for providing electrical power to the modules as well as signal lines for conveying information and data. Such an arrangement is satisfactory in a situation where the modules and the back plane or motherboard remain spatially fixed relative to one another when in operation. However, complications can arise when the modules need to spatially moved relative to the back plane or motherboard when in use. A common contemporary approach to addressing such complications is to employ flexible leads for conveying power to the modules and coupling data signals to and from the modules.

A problem with such flexible leads is that their conductors can work-harden, namely develop fatigue cracks, which can result in fracture and hence in at least partial loss of electrical connection. Another problem is that such flexible leads are often an inconvenience in that they can obstruct desired movement. In contemporary systems requiring appreciable electrical power transfer, flexible leads can become impractically bulky.

In a technical article "Optimized Linear Contactless Power Transmission Systems for Different Applications" by J. M. Barnard et al., 1997 IEEE, linear contactless power transmission systems are described as alternative power supplies to mobile loads. Such systems are elucidated each to comprise an extended primary winding provided with a core slidable in operation along the extended primary winding, the core itself including a secondary winding. The core is fabricated from a material exhibiting a relative magnetic permeability, which is considerably greater than unity for concentrating magnetic flux generated by the primary winding in operation within the core. In operation, alternating electrical power is coupled from the primary winding to the secondary winding. In mining applications in which the contactless power transmission systems are required to transfer up to 15 kW of power there through, the primary winding can have a length approaching substantially 5 meters. These contactless systems are considered in the article only for use in the contactless transfer of power in alternating form from the primary winding to the secondary winding.

When a variable load is coupled to the secondary winding, for example a variable load coupled via switching thyristors or switching power transistor devices for controlling power to the load in a pulse width modulated (PWM) mode of operation, transient surges of power are encountered at the primary winding and can cause potential interference. Such interference can be especially a problem in a situation wherein the load is at least in part digital hardware whose operation is adversely affected by such transient surges; such transient surges can result in data errors and associated consequential malfunction. Moreover, such interference is especially pertinent if a data control signal is communicated via the core concurrently with power being transferred through the core.

A known solution to this problem of interference caused by power transients to data signals is addressed by communicating data via a first medium, for example by optical fiber or wireless, and coupling power via a second medium, for example magnetically as described in the foregoing. However, such solutions can potentially give rise to increased system complexity or potential unreliability in a situation wherein data communication is implemented via wireless, for example WLAN, on account of potential sporadic radio interference. Such an issue of data reliability is especially pertinent in safety-critical applications when controlling powerful apparatus, for example mining equipment, or providing vital functions as in hospital environments.

In view of magnetic coupling being a relatively reliable approach to transfer power and data, it has been appreciated that magnetic couplers can be designed that are operable to at least partially isolate power transfer and data transfer. One approach is to use mutually isolated first and second magnetic couplers for power transfer and data transfer within systems respectively. Such an approach is described in a published U.S. Pat. No. 5,229,652, wherein there is disclosed a non-contact way to provide electrical power and two-way digital communications between a host computer and its peripheral modules; such peripheral modules include, for example, IC memory cards, modems and A/D converters. A magnetic core is employed to provide efficient transfer of both large amounts of electrical power and high-speed digital communications through transformer action. Peripheral modules requiring different power supply voltages or different data voltage levels can be accommodated and intermixed with modules of other types in a same host system. The connector includes detent structures to align the assembly in three dimensions, both upon mating, and under mechanical environmental stress conditions during operation. The magnetic core is provided with both power supply and data windings, the data winding has sections of opposite polarity so that the power supply signal imposed on the data winding cancels itself.

A problem with an approach as described in the aforementioned U.S. Pat. No. 5,229,652 is that inclusion of the detect structures and the implementation of the magnetic core do not allow for relative spatial movement in a manner akin to that described in the aforementioned technical article. Such inability to allow for relative spatial movement whilst providing mutually isolated transformer coupling of electrical power signals and data signals is a technical problem addressed by the present invention.

The present invention is thus directed to at least partially address the aforementioned problem.

SUMMARY OF THE INVENTION

An object of the present invention is to provide a coupling system which is operable to accommodate relative spatial movement of coupling components whilst also providing for relative isolation of electrical power and data signals conveyed through the coupling components.

According to a first aspect of the present invention, there is provided a coupling device comprising at least first and second mutually complementary magnetic cores configured to form in operation a magnetic circuit, said magnetic circuit being provided with a first set of electrical windings for magnetically coupling a first electrical signal through the device by way of a first magnetic path in the circuit, said circuit being provided with a second set of electrical windings for magnetically coupling a second electrical signal through the device by way of a second magnetic path in the circuit, said first and second paths partially spatially intersecting, and said first and second sets of windings being configured so that:

(a) the first set of windings is substantially sensitive to magnetic flux established in operation in the first magnetic path, and substantially insensitive to magnetic flux established in operation in the second magnetic path; and (b) the second set of windings is substantially sensitive to magnetic flux established in operation in the second magnetic path, and substantially insensitive to magnetic flux established in operation in the first magnetic path;

wherein said at least first and second magnetic cores are configured so as to enable in operation relative motion there between with their associated windings whilst magnetically coupling said first and second signals through the circuit.

The invention is of advantage in that the device is capable of coupling both electrical power and data signals there through with relatively low mutual crosstalk and yet accommodating relative motion of cores of the device.

Optionally, in the device, said at least first and second magnetic cores each include a plurality of limbs projecting from a base, said plurality of limbs on said first magnetic core being elongate substantially in a first direction, and being operable to support motion there along of the second core relative to the first core in said first direction whilst magnetically coupling said first and second signals through the circuit.

Optionally, in the device, each of said at least first and second magnetic cores includes a base having projecting there from a central limb and a plurality of side limbs neighboring thereto, said central limb being operable to provide said second magnetic path, and said first magnetic path substantially circumventing said central limb and passing via said plurality of side limbs.

Optionally, in the device, at least one of said at least first and second magnetic cores is implemented as a substantially elongate component for supporting in operation said motion there along.

Optionally, in the device, said at least first and second magnetic cores are implemented as cores having a substantially "E"-shaped cross-section.

Optionally, in the device, said first and second magnetic cores are each implemented from a magnetic material having a relative permeability substantially at least an order of magnitude greater than unity.

According to a second aspect of the invention, there is provided a coupling system including a coupling device according to the first aspect of the invention, wherein said system includes signal generating means for generating a first signal, and rectifying means for rectifying said first signal magnetically coupled in operation through said device, said first signal being configured to provide an electrical power supply via the rectifying means.

Optionally, in the coupling system, said system further includes data processing means operable to provide unidirectional or bidirectional data communication via a second signal magnetically coupled in operation through said device.

According to a third aspect of the invention, there is provided a method of magnetically coupling first and second signals through a coupling device, said device comprising at least first and second mutually complementary magnetic cores configured to provide in operation a magnetic circuit, said circuit being provided with a first set of electrical windings and a second set of electrical windings for magnetically coupling first and second signals respectively through said coupling device, said method including steps of:

(a) applying said first signal to said first set of electrical windings for magnetically coupling said first electrical signal through the device by way of a first magnetic path in the circuit; and (b) applying said second signal to said second set of the electrical windings for magnetically coupling said second electrical signal through the device by way of a second magnetic path in the circuit, wherein said first and second set of windings are configured so that:

(c) the first set of windings are substantially sensitive to magnetic flux established in operation in the first magnetic path, and substantially insensitive to magnetic flux established in operation in the second magnetic path; and (d) the second set of windings are substantially sensitive to magnetic flux established in operation in the second magnetic path, and substantially insensitive to magnetic flux established in operation in the first magnetic path;

wherein said first and second magnetic paths are partially spatially intersecting, and said at least first and second magnetic cores are configured to enable in operation relative motion there between with their associated windings whilst magnetically coupling said first and second signals through the circuit.

According to a fourth aspect of the invention, there is provided a medical system including a carrier for receiving a subject, said carrier being provided substantially along at least one peripheral edge thereof with at least one device according to the first aspect of the invention for magnetically coupling first and second signals there through to system apparatus, said first and second signals being magnetically coupled through said at least one device substantially without crosstalk arising in operation between said first and second signals.

Optionally, in the medical system, the first signal is a power supply signal and the second signal is a data signal.

Optionally, in the medical system, the first and second signals both include data signals or the first and second signals both include power supply signals.

Optionally, in the medical system, said at least one device is implemented at least in part in elongate form along said at least one peripheral edge of said carrier so as to accommodate in operation repositioning and mounting of said apparatus along said at least one device.

Optionally, in the medical system, said carrier is of elongate form including two lateral peripheral edges and two end edges, wherein said at least one device is implemented along at least one of said two lateral peripheral edges and said two end edges.

Optionally, in the medical system, said at least one device is detachable from said carrier.

Optionally, in the medical system, said at least one device is operable to enable said apparatus to mutually exchange data in operation whilst also providing a power supply to said apparatus. Moreover, the medical system is optionally configurable so that data flow to the apparatus is either optionally bi-direction or uni-directional. Furthermore, the medical system is also optionally configurable merely to provide a power supply to apparatus included therein and not convey data thereto or there from.

According to a fifth aspect of the invention, there is provided a vehicle including a coupling device according to the first aspect of the invention for providing a magnetic data signal and a power supply coupling to units included in said vehicle. More optionally, in the vehicle, said units include at least one of: vehicle seats, rotatable engine or engine transmission units.

According to a sixth aspect of the invention, there is provided a domestic appliance including a coupling device according to the first aspect of the invention for providing a magnetic data signal and a power supply coupling to units compatible with said appliance.

It will be appreciated that features of the invention are susceptible to being combined in any combination without departing from the scope of the invention as defined by the accompany claims.

BRIEF DESCRIPTION OF THE FIGURES

Embodiments of the present invention will now be described, by way of example only, with reference to the accompanying drawings wherein:

FIG. 1 is a schematic illustration of a coupling device for a coupling system pursuant to the present invention, the device including a housing, a first elongate magnetic E-shaped core included within the housing, and a second magnetic E-shaped core operable to be moved along the first core in a linear sliding manner with end members of the first and second cores mutually facing and aligning to facilitate magnetic flux coupling there between;

DESCRIPTION OF EMBODIMENTS OF THE INVENTION

In describing the present invention, a coupling system will be described and then various diverse practical applications of the coupling system will be described.

Figure 1:
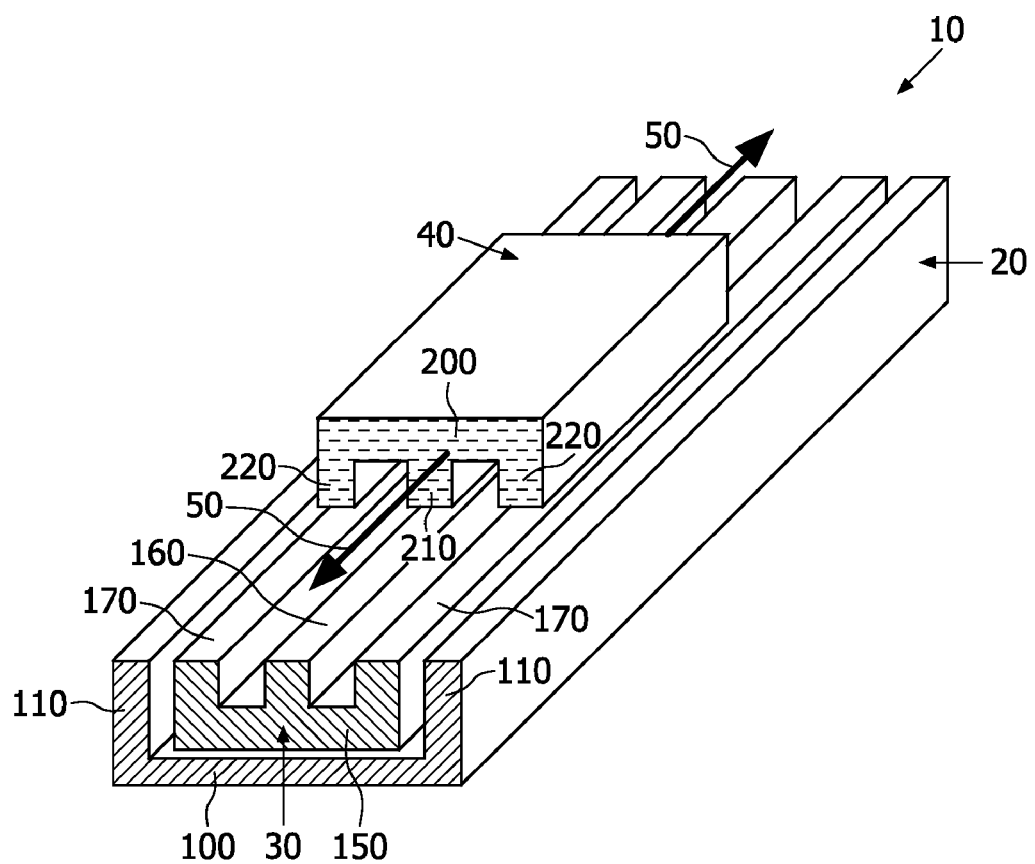

Referring to FIG. 1, there is shown a magnetic coupling device adapted for implementing a coupling system pursuant to the present invention. The magnetic coupling device is indicated generally by 10. The device 10 comprises an elongate housing 20, a first core 30 and a second core 40. The second core 40 is operable to be moved in operation in directions denoted by arrows 50 relative to the first core 30 so that complementary limbs of the cores 30, 40 remain mutually aligned.

The housing 20 is implemented as a "U"-shaped channel having a base 100 and two side walls 110. Optionally, the channel is fabricated from a plastics material, an extruded non-ferrous metal such as aluminum (aluminum), non-magnetic stainless steel, or from a ceramic material. The housing 20 is operable to accommodate therein the first core 30 implemented as an elongate component and optionally fabricated from one or more abutting "E"-shaped cross-section sections of magnetic material having a relative magnetic permeability $\mu_r$ at least an order of magnitude greater than unity; optionally, the relative magnetic permeability $\mu_r$ is in a range of substantially 10 to 1000. The magnetic material is beneficially selected to exhibit low hysteresis losses at higher frequencies so as to support a relative high data communication bandwidth through the device 10, for example at least several MegaHertz (MHz) bandwidth; for example, the high relative permeability magnetic material optionally comprises ferrite material or thin metal silicon steel sheets or wires stacked and bonded together. The first core 30 is of substantially "E"-shaped cross-section comprising a base 150, a central limb 160 centrally projecting from the base 150 and two outer limbs 170 also projecting from the base 150, the outer limbs 170 each neighboring to the central limb 160 as illustrated. The base 150 and its associated limbs 160, 170 are optionally mutually unitary. Moreover, the first core 30 is beneficially both magnetically and spatially symmetrical about a longitudinal axis of the central limb 160 as illustrated. The base 150 of the first core 30 is operable to abut onto the base 100 of the housing 20 as illustrated for accommodating the first core 30 into the housing 20; the housing 20 is thereby operable to provide mechanical support and protection to the first core 30. Optionally, the first core 30 can be embedded in the housing 20, for example by way of resin potting or injecting silicone rubber or similar highly compliant material. Exposed end faces of the limbs 160, 170 are optionally mutually parallel and equidistant from a plane including a remote side of the base 150 abutting onto the housing 20, although such a requirement for parallelism is not essential for the present invention to function.

The device 10 further comprises a second core 40 which is also beneficially of substantially "E"-shaped cross-section and substantially complementary in cross-section to the first core 30. The second core 40 is also optionally of elongate form as illustrated and comprises one or more mutually abutting sections. Moreover, the second core 40 includes a base 200, a central limb 210 projecting from the base 200 and two side limbs 220 projecting from the base 200 as illustrated; the two side limbs 220 each neighbor onto the central limb 210. The second core 40 is fabricated from a magnetic material in a similar manner to the first core 30 as described in the foregoing.

In operation, the device 10 is disposed such that the limbs 160, 170 of the first core 30 are in contact or near proximity to the limbs 210, 220 of the second core 40 in a manner as illustrated in FIGS. 1 to 4. Beneficially, in operation, a gap distance between the opposing external faces of the limbs 160, 210, similarly a corresponding gap distance between the opposing external faces of the limbs 170, 220 should be substantially at least an order of magnitude smaller than, for example, a lateral width of the bases 150, 200, so as to limit magnetic flux fringing at the external faces of the limbs 160, 170, 210, 220 to a manageable degree.

Figure 2:
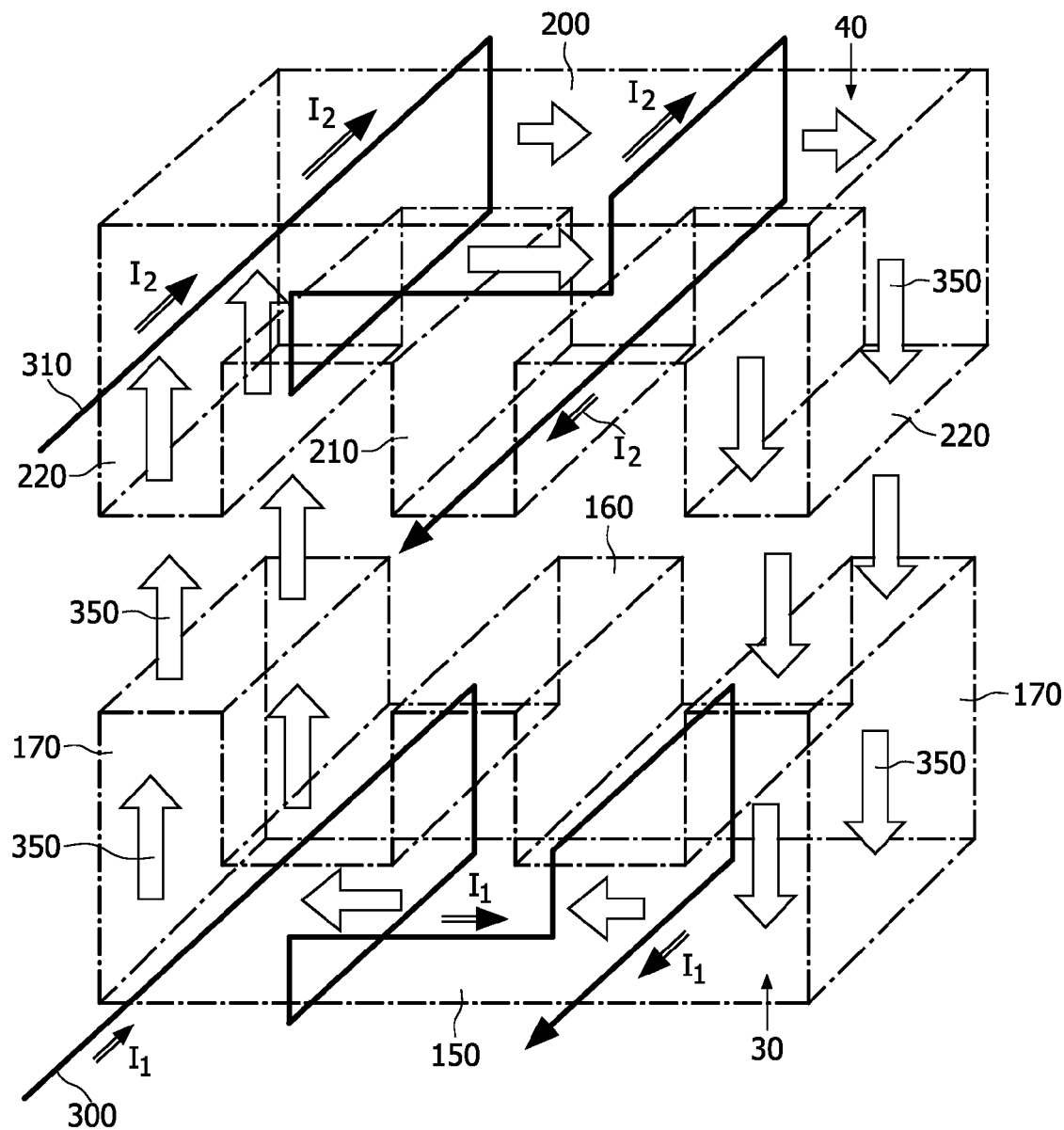
FIG. 2 is a schematic illustration of coupling, via a first path through the first and second magnetic cores of FIG. 1, a magnetic flux induced in the first core to the second core.
Figure 3:
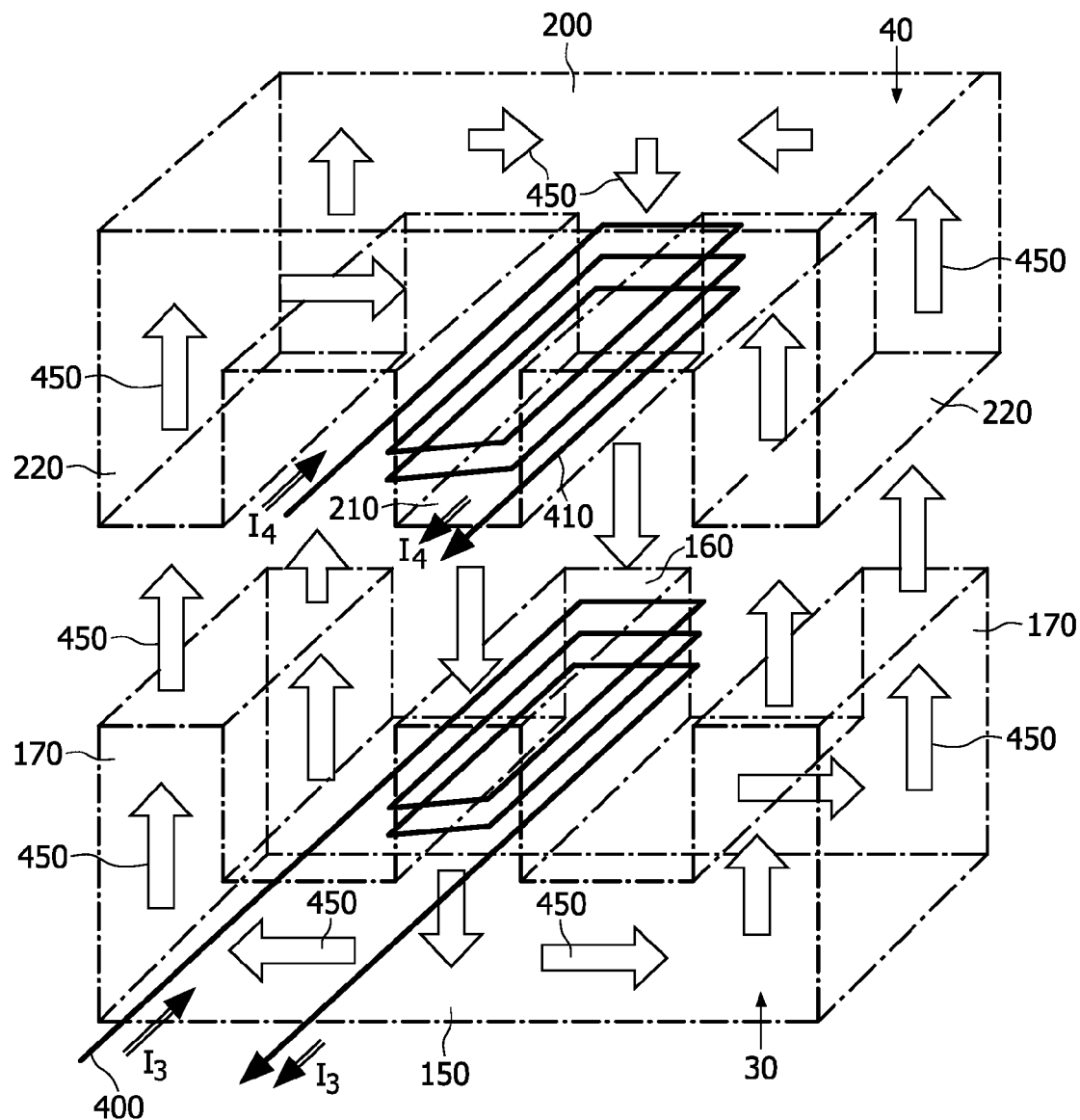
FIG. 3 is a schematic illustration of coupling, via a second path through the first and second magnetic cores of FIG. 1, a magnetic flux induced in the first core to the second core.
Figure 4:
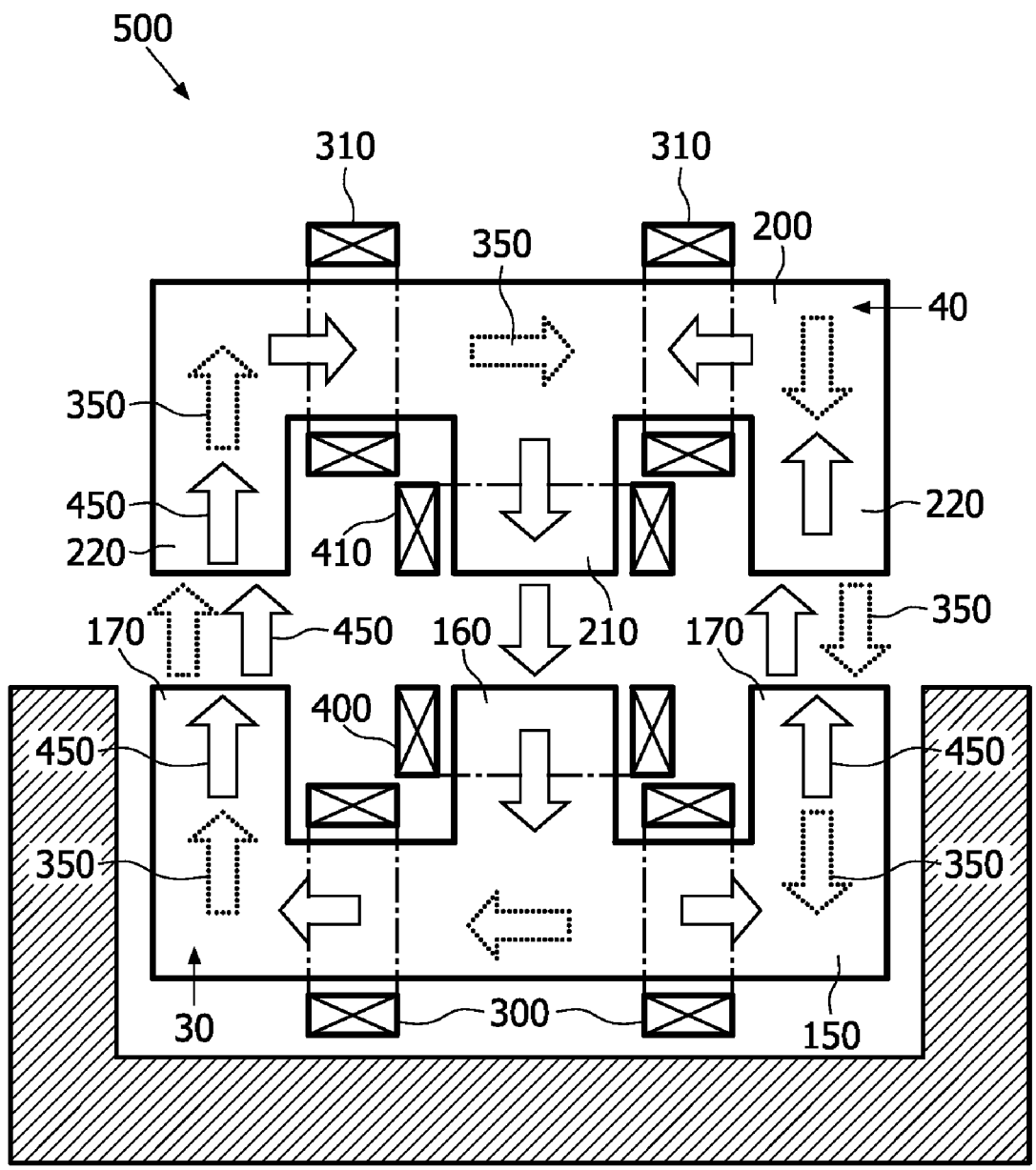
FIG. 4 is a schematic illustration including details from FIGS. 2 and 3 illustrating juxtaposition of windings included on the first and second cores illustrated in FIG. 1.

The cores 30, 40 are operable to mutually co-operate so that:

(a) a first magnetic field induced by a first primary winding 300 included on the first core 30 is operable to couple to a first secondary winding 310 included on the second core 40 via a first magnetic path comprising the bases 150, 200 and the outer limbs 170, 220 with substantially negligible magnetic flux coupling via the central limbs 160, 210; the first magnetic path is defined substantially by arrows 350 illustrated in FIGS. 2 and 4; and (b) a second magnetic field induced by a second primary winding 400 included on the first core 30 is operable to couple to a second secondary winding 410 included on the second core 40 via a second magnetic path comprising the central limbs 160, the bases 150, 200 and the outer limbs 170, 220, the second magnetic path is defined substantially by arrows 450 in FIGS. 3 and 4.

The first primary and secondary windings 300, 310 are formed onto the first and second cores 30, 40 respectively so that they are mutually substantially insensitive to magnetic fields established along the second magnetic path denoted by the arrows 450 in FIG. 3. Similarly, the second primary and secondary windings 400, 410 are formed onto the first and second cores 30, 40 respectively so that they are mutually substantially insensitive to magnetic fields established along the first magnetic path denoted by the arrows 350 in FIG. 2. Thus, the first windings 300, 310 are susceptible to coupling electrical power via the cores 30, 40 substantially without coupling occurring to the second windings 400, 410; similarly, the second windings 400, 410 are susceptible to coupling data signals via the cores 30, 40 substantially without coupling occurring to the first windings 300, 310. Alternatively, the first windings 300, 310 are susceptible to coupling data signals via the cores 30, 40 substantially without coupling occurring to the second windings 400, 410; similarly, the second windings 400, 410 are susceptible to coupling electrical power via the cores 30, 40 substantially without coupling occurring to the first windings 300, 310. The cores 30, 40 are thereby operable to convey both electrical power and data signals there through without cross-talk occurring there between. Moreover, synergistically, the cores 30, 40 are also operable to provide such mutually-isolated coupling of electrical power and data signals there through whilst the second core 40 is moved relative to the first core 30 in longitudinal directions as denoted by the arrows 50 included in FIG. 1.

In order that the present invention be more fully and completely described, implementations of the first windings 300, 310 and the second windings 400, 410 will now be further elucidated with reference to FIGS. 2 and 3 respectively.

In FIG. 2, the first primary winding 300 is shown routed from a start point via a first gap between the central limb 160 and a first of the side limbs 170, then around a rear of the base 150 and halfway up the base 150 again towards the start point, then transversely towards a second gap between the central limb 160 and a second of the side limbs 170, via the second gap and then around the rear of the base 150. Moreover, the first secondary winding 310 is routed from a start point via a rear of the base 200 around to a third gap between a first of the side limbs 220 and the central limb 210, then half back towards the start point, then in a direction towards a fourth gap between the second of the side limbs 220 and the central limb 210, thereafter around the rear of the base 200, and then via the fourth gap out. A current $I_1$ applied to the first primary winding 300 is operable to establish the magnetic field denoted by the arrows 350 around the aforementioned first magnetic path, the first magnetic path not substantially including the central limbs 160, 210; the current $I_1$ flowing in the first primary winding 300 is operable to induce a corresponding current $I_2$ in the first secondary winding 310. It will be appreciated from FIGS. 2 and 4 that the first primary and secondary windings 300, 310 are disposed so as to be in a non-opposing manner on the bases 150, 200 and/or the side limbs 170, 220 to establish the magnetic field around the aforementioned first magnetic path denoted by the arrows 350. The first primary and secondary windings 300, 310 are optionally implemented as single-turn windings; alternatively, one or more of the first primary and secondary windings 300, 310 are optionally implemented as multi-turn windings, for example to provide voltage step-up or voltage step-down properties as required for the device 10.

In FIG. 3, the second primary winding 400 is routed as one or more turns around the central limb 160 of the first core 30 as illustrated. Similarly, the second secondary winding 410 is routed as one or more turns around the central limb 210 of the second core 40 as illustrated. A current $I_3$ applied to the second primary winding 400 is operable to establish the magnetic field denoted by the arrows 450 around the aforementioned second magnetic path, the second magnetic path having associated therewith a magnetic flux through the central limbs 160, 210 in a mutually opposite spatial direction relative to a corresponding magnetic flux through the side limbs 170, 220. The current $I_3$ flowing in the second primary winding 400 is operable to induce a corresponding current $I_4$ in the second secondary winding 410. It will be appreciated from FIGS. 3 and 4 that the second primary and secondary windings 400, 410 are disposed so as to establish the magnetic field around the aforementioned second magnetic path denoted by the arrows 450. The second primary and secondary windings 400, 410 are optionally implemented as single-turn windings; alternatively, one or more of the second primary and secondary windings 400, 410 are optionally implemented as multi-turn windings, for example to provide voltage step-up or voltage step-down properties as required for the device 10.

One or more of the windings 300, 310, 400, 410 can be implemented as windings fabricated from electrically conductive wire provided with external insulation, for example enamel or plastics material insulation. Alternatively, one or more of the windings 300, 310, 400, 410 can be implemented as conductive metallic film or strip conductors electrically insulated by embedding them in flexible insulating film, for example Kapton or similar polyamide and/or polyester plastics material film. Other implementations of the windings 300, 310, 400, 410 are feasible and are to be construed to be within the scope of the present invention; such other implementations include printed windings including conductive paths printed or otherwise formed onto single or multilayer printed circuit boards.

The device 10 depicted in FIGS. 1 to 4 is beneficially included as part of a coupling system for providing simultaneous magnetic coupling of electrical power and data signals without substantial cross-talk and mutual interference occurring. Thus, the device 10 is beneficially provided with one or more electronic circuits to implement a corresponding coupling system wherein the electronic circuits are operable to provide rectification of electrical power coupled through the device 10, and to isolate and optionally demodulate data signals coupled through the device 10.

There is potentially an enormous range of practical applications for the device 10, such applications including but not limited to:

(a) wireless power transmission in machines, for example component placement machines and robots, the device 10 being operable to reduce friction and circumvent potential failure by work-hardening effects; magnetic coupling pursuant to the present invention can be implemented in linear or curvi-linear form, namely the first core 30 can be implemented in either a linear or curved manner as required depending on a form of motion to be accommodated in such machines;

(b) in industrial printers and laser cutting machines wherein a head including electronic components, and optionally also optical components, is to be moved rapidly and repeatedly in relation to a work-piece;

(c) in household power-transfer applications, for example in a kitchen or bathroom dresser; a kitchen cooker can, for example, be implemented using the devices 10, wherein saucepans and frying pans include resistive heating elements operable to be driven by power transfer through one or more of the devices 10 included in a hob region of the cooker and in the saucepans and frying pans; the saucepans and frying pans are beneficially provided with temperature control implemented by way of temperature sensors and boil-over sensors incorporated therein, these sensors being operable to communicate in digital mode back through the one or more devices 10 to a central control unit of the cooker for boil-over warning or temperature control purposes;

(d) in machine tools such as lathes wherein a linearly actuated tool turret is to be provided locally with power, for example to energize monitoring and measurement sensors, the device 10 in such application being potentially relatively immune to debris arising from machining operations;

(e) in medical applications such as intensive-care beds wherein vital life-support apparatus is to be provided in operation with electrical power as well as there being provided bi-directional data communication to and from such apparatus; such intensive care beds need to provide nursing staff and medical doctors with optical patient access with only a limited encumbrance of flexible leads and similar obstructions. Moreover, the apparatus needs to be repositionable along such intensive-care beds without an interruption in electrical supply or data communication occurring. Furthermore, such apparatus can include vital monitoring and/or diagnostic equipment, for example heart-beat monitors, blood-pressure monitors, respiration monitors, heart-bypass pumps, surgical lasers, cauterizing equipment, robotic endoscopy equipment, actuated endoscopy cameras, X-ray examination apparatus, CT-scanners, magnetic resonance imaging systems, nuclear medicine systems, ultrasonic scanning probes, drug delivery equipment, dialysis units, blood aeration monitors to mention just a few examples. Such apparatus not only needs to be provided with power but has a need to be supported with bi-directional data communication, for example a video link when the apparatus is to be operated by a surgeon or physician located remotely from such intensive-care beds; and (f) in automotive applications, for example in a situation wherein a passenger seat is mounted on guides such that the first core 30 and its associated second core 40 can be mounted parallel to or concurrently with one or more of the guides, thereby providing the passenger seat with electrical functionality such as in-seat heating, motor-actuated seat adjustment, audio-visual seat facilities such as in-built LCD video screen, radio, and yet supporting linear sliding adjustment of the passenger seat on its guides.

Figure 5:
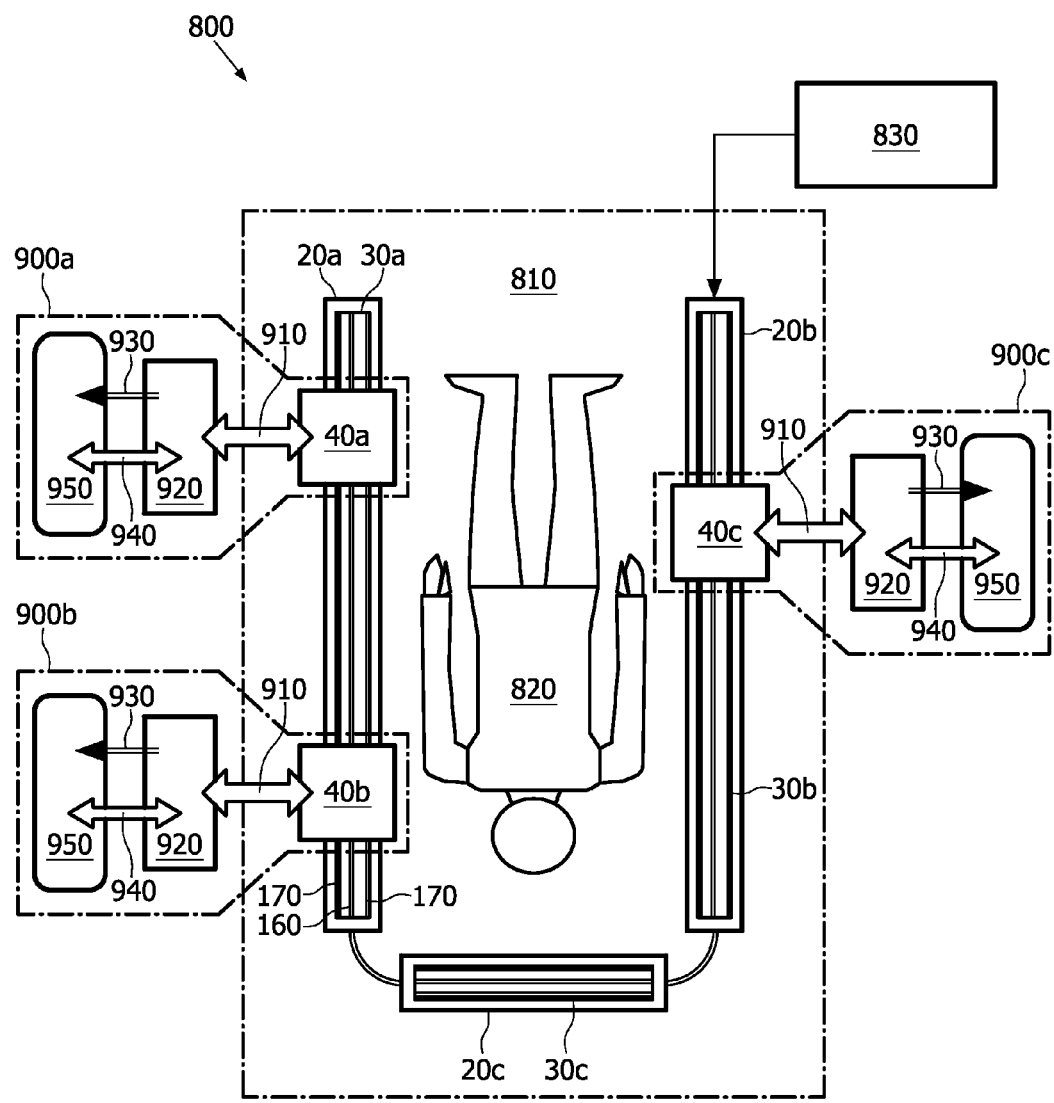
FIG. 5 is a simplified schematic illustration of a medical system including coupling devices substantially as illustrated in FIGS. 1 to 4 pursuant to the present invention; the medical system is adapted to receive a subject such as a human being; the coupling devices enable power supply and data signals to be coupled to apparatus of the medical system such that the apparatus are spatially movable within the medical system on account of use of the coupling devices.

In FIG. 5, there is shown a medical system indicated generally by 800. The medical system 800 comprises a bed 810 for receiving a subject 820, for example a human patient; the bed 810 is optionally an intensive-care bed as described in paragraph (e) in the foregoing or an operating-theatre bed. The bed 810 includes at peripheral regions thereof first and second housings 20a, 20b with corresponding first cores 30a, 30b respectively; the first cores 30a, 30b are similar to the aforementioned core 30 illustrated in FIGS. 1 to 4 or elucidated variants thereof. Moreover, the bed 810 further includes at its first end an end housing 20c provide with its associated first core 30c; the core 30c is similar in design to the cores 30a, 30b but of shorter longitudinal length. The cores 30a, 30b, 30c are mutually coupled together by way of corner couplings so that the cores 30a, 30b, 30c are capable of operating as a common electrical power source and also as a data bus operable to support single-direction or bi-direction data communication there through. The end housing 20c and its core 30c are optionally only included at the first end of the bed 810, for example near feet of the subject 820 as illustrated, so as to provide access for physically lifting the subject 820 onto and away from the bed 810. Optionally, a second end of the bed 810 opposite the first end thereof can be additionally provided with an end housing and associated first core so that the subject 810 is fully surrounded with first cores mounted in associated housings. Yet more optionally, one or more of the housings 20a, 20b, 20c and their first cores 30a, 30b, 30b can be rendered detachable from the bed 810 for purposes or substantially reconfiguring the bed 810.

The housing 20a, 20b, 20c and their first cores 30a, 30b, 30c are susceptible to being mutually coupled in a series manner using aforementioned corner couplings as illustrated in FIG. 5; alternatively, a parallel manner of mutually coupling the housings 20a, 20b, 20c and their associated first cores 30a, 30b, 30c is optionally employable.

The cores 30a, 30b, 30c are coupled to an interface 830. The interface 830 includes a high-frequency oscillator (not shown) for driving the first primary windings 300 of the first cores 30a, 30b, 30c for electrical power supply purposes within the medical system 800; the oscillator is optionally supplied with mains electricity via an uninterruptible power supply so that operation of the bed 810 is maintained in an event of mains power fail. Moreover, the oscillator is optionally implemented to operate in a frequency range of 1 kilohertz to 1 MegaHertz, and more optionally in a range of 20 kilohertz to 100 kilohertz. Electrical power coupled from the first cores 30a, 30b, 30c to corresponding first secondary windings 310 of second cores 40a, 40b, 40c is operable to power apparatus 900a, 900b, 900c included in the medical system 800. On account of the first cores 30a, 30b, 30c being elongate in form, the second cores 40a, 40b, 40c respectively are slidably displaceable in operation along the first cores 30a, 30b, and 30c whilst maintaining operation of the apparatus 900a, 900b, and 900c respectively as will be elucidated later.

The interface 830 is shown coupled to the first core 30b via power connections 850 and data connections 840; the first core 30b is shown coupled by way of corner couplings in series via the first core 30c to the first core 30a. Moreover, the interface is shown also coupled via a data connection 860 to a remote data system 870. The remote data system 870 is beneficially a hospital database which optionally itself is coupled to other communication networks, for example to the Internet for accessing patient records pertaining to the subject 820.

The apparatus 900a, 900b, 900c will now be further elucidated. Each apparatus 900a, 900b, 900c comprises its associated second core 40a, 40b, 40c respectively. Each apparatus 900a, 900b, 900c includes a rectifier unit 920 coupled via a connection 910 to the windings 310, 410 of its associated second cores 40*a*, 40*b*, 40*c* respectively. Moreover, each rectifier unit 920 includes a power output 930 for powering its associated functional unit 950, and also a bi-directional or uni-directional data output/input 940 for providing data to or conveying data from the associated functional unit 950. The rectifier units 920 are operable to rectify alternating signals generated by the oscillator of the interface 830 and coupled via the first windings 300, 310 of the coupling devices 10 included by way of the cores 30*a*, 30*b*, 30*c*, 40*a*, 40*b*, 40*c* to generate an electrical voltage for energizing the functional units 950. Moreover, the rectifier units 920 are also operable to couple data signals coupled via the second windings 400, 410 of the coupling devices 10 so as to couple the functional devices 950 to a data bus in the medical system 800 provided by way of the devices 10. Optionally, the functional units 950 are provided with other modes of communication, for example wireless local area network (WLAN), for non-critical data. Beneficially, safety-critical or life-critical data flow is implemented via the devices 10 of the medical system 800.

Although three apparatus 900*a*, 900*b*, 900*c* are illustrated in FIG. 5, it will be appreciated that one or more such apparatus 900*a*, 900*b*, 900*c* are optionally included in response to operating or care requirements for the subject 820. More optionally, such apparatus 900*a*, 900*b*, 900*c* can be removed or introduced to the first cores 30*a*, 30*b*, 30*c* as required during care or analysis of the subject 820; for example, various apparatus 900*a*, 900*b*, 900*c* are selectively introduced or removed from the bed 810 in response to improvement or deterioration in a condition of the subject 820.

By way of the second primary and secondary windings 400, 410 included on the first cores 30*a*, 30*b*, 30*c* and their associated second cores 40*a*, 40*b*, 40*c* respectively, high reliable unidirectional or bidirectional data communication is supported in the medical system 800. For example, two of more of the apparatus 900*a*, 900*b*, and 900*c* are susceptible to mutually communicating data there between via their associated devices 10. Moreover, one or more of the apparatus 900*a*, 900*b*, and 900*c* is optionally susceptible to communicating by bidirectional or unidirectional communication with the interface 830, for example:

(a) for receiving external instructions from a doctor or physician remote from the system 800; and/or (b) for accessing a remote database, for example data records recorded on a hospital or patient database, for example stored in the remote data system 870.

The medical system 800 can be implemented as a retrofit to existing beds in hospitals or clinics. Moreover, the medical system 800 is susceptible to being modified for use in dentistry wherein various apparatus 900 such as dental drills, suction pumps, cauterizers, UV light sources for curing dental resin and X-ray equipment need to be readily available to a dentist to support optimal patient treatment efficiency; obstruction caused by various cables is potentially thereby circumvented by utilizing one or more of the devices 10.

As a potential modification of the device 10, the second core 40 can be optionally formed into a circular rim wherein external surfaces of the limbs 210, 220 face radially outwardly, for example in a curvi-linear manner. Moreover, in such an embodiment of the invention, the first core 30 can be implemented to be mounted so that external faces of its limbs 160, 170 face radially inwardly a small radial distance away towards the radially outwardly facing external surfaces of the limbs 210, 220 respectively. The cores 30, 40 so implemented enable the device 10 to function as a radial magnetic coupler for coupling power and bidirectional signals to the second core 40 mounted onto a revolving component. This embodiment is susceptible to being used in rotating machinery, for example in automotive applications wherein electronic transmission and coupling is utilized in vehicles. Alternatively, such an embodiment is also capable of being adapted for use with turbines of aero-engines wherein high reliability and robustness is paramount. Alternatively, marine engines can be adapted to utilize such a modified rotary implementation of the device 10.

Although the first and second cores 30, 40 of the device 10 as described in the foregoing are each provided with three limbs for enabling two mutually different magnetic paths to be established within the device 10 in operation, so that two electrical signals can be conveyed with relatively insignificant mutual cross-talk there between through the device 10, it will be appreciated that the first and second cores 30, 40 can be modified to include more than three limbs each. For example, the cores 30, 40 can be modified to include five limbs each so as to enable three mutually different magnetic paths to be established through the device 10; the device 10 thus modified can convey there through three electrical signals with relatively insignificant mutual cross-talk.

Modifications to embodiments of the invention described in the foregoing are possible without departing from the scope of the invention as defined by the accompanying claims.

Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural.

Numerals included within parentheses in the accompanying claims are intended to assist understanding of the claims and should not be construed in any way to limit subject matter claimed by these claims.

The invention claimed is:

1. A coupling device comprising at least first and second mutually complementary magnetic cores configured to form in operation a magnetic circuit, said magnetic circuit being provided with a first set of electrical windings for magnetically coupling a first electrical signal through the device by way of a first magnetic path in the circuit, said circuit being provided with a second set of electrical windings for magnetically coupling a second electrical signal through the device by way of a second magnetic path in the circuit, said first and second paths partially spatially intersecting, said first and second sets of windings being configured so that:

(a) the first set of windings is substantially sensitive to magnetic flux established in operation in the first magnetic path, and substantially insensitive to magnetic flux established in operation in the second magnetic path; and (b) the second set of windings is substantially sensitive to magnetic flux established in operation in the second magnetic path, and substantially insensitive to magnetic flux established in operation in the first magnetic path; and wherein said at least first and second magnetic cores are configured so as to enable in operation relative motion there between with their associated windings whilst magnetically coupling said first and second signals through the circuit.

2. A coupling device as claimed in claim 1, wherein said at least first and second magnetic cores each include a plurality of limbs projecting from a base, said plurality of limbs on said first magnetic core being elongate substantially in a first direction, and being operable to support motion there along of the second core relative to the first core in said first direction whilst magnetically coupling said first and second signals through the circuit.

3. A coupling device as claimed in claim 1, wherein each of said at least first and second magnetic cores includes a base having projecting there from a central limb and a plurality of side limbs neighboring thereto, said central limb being operable to provide said second path magnetic path, and said first magnetic path substantially circumventing said central limb and passing via said plurality of side limbs.

4. A coupling device as claimed in claim 1, wherein at least one of said at least first and second magnetic cores is implemented as a substantially elongate component for supporting in operation said motion there along.

5. A coupling device as claimed in claim 1, wherein said at least first and second magnetic cores are implemented as cores having a substantially "E"-shaped cross-section.

6. A coupling device as claimed in claim 1, wherein said at least first and second magnetic cores are each implemented from a magnetic material having a relative permeability substantially at least an order of magnitude greater than unity.

7. A coupling system including a coupling device as claimed in claim 1, wherein said system includes signal generating means for generating a first signal, and rectifying means for rectifying said first signal magnetically coupled in operation through said device, said first signal being configured to provide an electrical power supply via the rectifying means.

8. A coupling system as claimed in claim 7, wherein said system further includes data processing means operable to provide uni-directional or bi-directional data communication via a second signal magnetically coupled in operation through said device.

9. A method of magnetically coupling first and second signals through a coupling device, said device comprising at least first and second mutually complementary magnetic cores configured to provide in operation a magnetic circuit, said circuit being provided with a first set of electrical windings and a second set of electrical windings for magnetically coupling first and second signals respectively through said coupling device, said method including steps of:
(a) applying said first signal to said first set of electrical windings for magnetically coupling said first electrical signal through the device by way of a first magnetic path in the circuit; and
(b) applying said second signal to said second set of the electrical windings for magnetically coupling said second electrical signal through the device by way of a second magnetic path in the circuit; and
wherein said first and second set of windings are configured so that:
(i) the first set of windings are substantially sensitive to magnetic flux established in operation in the first magnetic path, and substantially insensitive to magnetic flux established in operation in the second magnetic path; and
(ii) the second set of windings are substantially sensitive to magnetic flux established in operation in the second magnetic path, and substantially insensitive to magnetic flux established in operation in the first magnetic path; and
wherein said first and second paths are partially spatially intersecting, and said at least first and second magnetic cores are configured to enable in operation relative motion there between with their associated windings whilst magnetically coupling said first and second signals through the circuit.

10. A medical system comprising:
a carrier for receiving a subject, said carrier being provided substantially along at least one peripheral edge thereof with at least one device for magnetically coupling first and second signals there through to system apparatus, said first and second signals being magnetically coupled through said at least one device substantially without crosstalk arising in operation between said first and second signals, said at least one device including at least first and second mutually complementary magnetic cores configured to form in operation a magnetic circuit, said magnetic circuit being provided with a first set of electrical windings for magnetically coupling a first electrical signal through the device by way of a first magnetic path in the circuit, said circuit being provided with a second set of electrical windings for magnetically coupling a second electrical signal through the device by way of a second magnetic path in the circuit, said first and second paths partially spatially intersecting, said first and second sets of windings being configured so that:
(a) the first set of windings is substantially sensitive to magnetic flux established in operation in the first magnetic path, and substantially insensitive to magnetic flux established in operation in the second magnetic path; and
(b) the second set of windings is substantially sensitive to magnetic flux established in operation in the second magnetic path, and substantially insensitive to magnetic flux established in operation in the first magnetic path; and
wherein said at least first and second magnetic cores are configured so as to enable in operation relative motion there between with their associated windings whilst magnetically coupling said first and second signals through the circuit.

11. A medical system as claimed in claim 10, wherein said first signal is a power supply signal and said second signal is a data signal.

12. A medical system as claimed in claim 10, wherein said first and second signals both include data signals or wherein said first and second signals both include power supply signals.

13. A medical system as claimed in claim 10, wherein said at least one device is implemented at least in part in elongate form along said at least one peripheral edge of said carrier so as to accommodate in operation repositioning and mounting of said apparatus along said at least one device.

14. A medical system as claimed in claim 10, wherein said carrier is of elongate form including two lateral peripheral edges and two end edges, wherein said at least one device is implemented along at least one of said two lateral peripheral edges and said two end edges.

15. A medical system as claimed in claim 10, wherein said at least one device is detachable from said carrier.

16. A medical system as claimed in claim 10, wherein said at least one device is operable to enable said apparatus to mutually exchange data in operation whilst also providing a power supply to said apparatus.

17. A vehicle comprising:
a coupling device for providing a magnetic data signal and a power supply coupling to units included in said vehicle, the coupling device including at least first and second mutually complementary magnetic cores configured to form in operation a magnetic circuit, said magnetic circuit being provided with a first set of electrical windings for magnetically coupling a first electrical signal through the device by way of a first magnetic path in the circuit, said circuit being provided with a second set of electrical windings for magnetically coupling a second electrical signal through the device by way of a second magnetic path in the circuit, said first and second paths partially spatially intersecting, said first and second sets of windings being configured so that:

(a) the first set of windings is substantially sensitive to magnetic flux established in operation in the first magnetic path, and substantially insensitive to magnetic flux established in operation in the second magnetic path; and (b) the second set of windings is substantially sensitive to magnetic flux established in operation in the second magnetic path, and substantially insensitive to magnetic flux established in operation in the first magnetic path; and wherein said at least first and second magnetic cores are configured so as to enable in operation relative motion there between with their associated windings whilst magnetically coupling said first and second signals through the circuit.

18. A domestic appliance comprising:

a coupling device for providing a magnetic data signal and a power supply coupling to units compatible with said appliance, the coupling device including at least first and second mutually complementary magnetic cores configured to form in operation a magnetic circuit, said magnetic circuit being provided with a first set of electrical windings for magnetically coupling a first electrical signal through the device by way of a first magnetic path in the circuit, said circuit being provided with a second set of electrical windings for magnetically coupling a second electrical signal through the device by way of a second magnetic path in the circuit, said first and second paths partially spatially intersecting, said first and second sets of windings being configured so that:

(a) the first set of windings is substantially sensitive to magnetic flux established in operation in the first magnetic path, and substantially insensitive to magnetic flux established in operation in the second magnetic path; and (b) the second set of windings is substantially sensitive to magnetic flux established in operation in the second magnetic path, and substantially insensitive to magnetic flux established in operation in the first magnetic path; and wherein said at least first and second magnetic cores are configured so as to enable in operation relative motion there between with their associated windings whilst magnetically coupling said first and second signals through the circuit.

* * * * *